United States Patent [19]

Shettigar et al.

[11] Patent Number: 5,211,850

[45] Date of Patent: May 18, 1993

[54] PLASMA FILTER SORBENT SYSTEM FOR REMOVAL OF COMPONENTS FROM BLOOD

[75] Inventors: Udipi Shettigar; James C. McRea, both of Midvale, Utah

[73] Assignee: Research Medical, Inc., Midvale, Utah

[21] Appl. No.: 736,405

[22] Filed: Jul. 26, 1991

[51] Int. Cl.⁵ .................. B01D 61/00; B01D 63/02
[52] U.S. Cl. .................. 210/645; 210/195.2; 210/257.2; 210/443; 210/500.23; 210/632; 210/646; 210/650; 210/651; 435/287; 435/288; 436/178; 604/4; 604/5
[58] Field of Search ............ 210/632, 637, 645, 646, 210/650, 484, 651, 483, 653, 443, 654, 444, 806, 257.2, 321.82, 321.83, 321.84, 321.85, 321.86, 321.87, 321.88, 321.89, 500.23, 502.1, 321.8, 321.81, 195.2; 604/4, 5, 6; 435/287, 288; 436/178, 177, 519, 529, 535

[56] References Cited

U.S. PATENT DOCUMENTS

| | | | |
|---|---|---|---|
| 3,742,946 | 9/1973 | Grossman | 210/321.87 |
| 4,025,436 | 3/1977 | Tsuda et al. | 210/321.8 |
| 4,045,352 | 8/1977 | Rembaum et al. | 210/500.23 |
| 4,075,100 | 2/1978 | Furuta et al. | 210/321.8 |
| 4,183,811 | 1/1980 | Walch et al. | 210/646 |
| 4,209,392 | 6/1980 | Wallace | 210/646 |
| 4,247,393 | 1/1981 | Wallace | 210/321.84 |
| 4,361,484 | 11/1982 | Larsson et al. | 210/321.65 |
| 4,578,191 | 3/1986 | Jaffrin et al. | 210/321.84 |
| 4,581,010 | 4/1986 | Skurkovich et al. | 604/4 |
| 4,619,639 | 10/1986 | Nosé et al. | 210/651 |
| 4,696,670 | 9/1987 | Ohnishi et al. | 210/340 |
| 4,698,155 | 10/1987 | Atkin | 210/500.23 |
| 4,863,611 | 9/1989 | Bernstein et al. | 210/661 |

OTHER PUBLICATIONS

S. F. Mohammad et al., Thrombosis Research, 20, pp. 599–609 (1980).

Primary Examiner—Robert A. Dawson
Assistant Examiner—Sun Uk Kim
Attorney, Agent, or Firm—Thorpe North & Western

[57] ABSTRACT

A system and method of achieving both convective and diffusive transport of plasma across a membrane accompanied by the selective removal of plasma components using sorbents followed by reinfusion of the purified plasma in a blood circulation system is achieved by pumping blood through a filter comprising a bundle of "U" shaped hollow fibers immersed in a closed plasma chamber containing sorbents in an electrolyte solution. As blood flows through the entry arm, due to positive transmembrane pressure difference, plasma filtration into the plasma chamber occurs. The entering plasma causes an increase in the chamber pressure but does not exceed the pressure in the entry arm. The increase in chamber pressure exceeds the pressure in the exit arm of filter where the transmembrane pressure difference is negative and the direction of filtration reverses causing reverse filtration/reinfusion of plasma from the chamber into the blood in the exit arm. The phenomena of positive and reverse filtration from the hollow fiber filter establishes the circulation of plasma fluid in the plasma chamber. The plasma filtering through the entry arm, which corresponds to the arterial end of the system, passes through the plasma chamber solution containing the sorbents where plasma components get selectively depleted. The sorbents may be in any usable form which are not permeable to the filter. The purified plasma reenters the filter along the exit arm corresponding to the venous end where negative transmembrane pressure exists.

23 Claims, 3 Drawing Sheets

PLASMA FILTER SORBENT SYSTEM FOR REMOVAL OF COMPONENTS FROM BLOOD

BACKGROUND OF THE INVENTION AND DESCRIPTION OF PRIOR ART

This to a system and method of achieving both convective and diffusive transport of plasma across a membrane accompanied by the selective removal of plasma components using sorbents, immobilized enzymes or antibodies followed by reinfusion of the purified plasma to a patient in an extracorporeal blood circulation system without using any plasma pump or transmembrane pressure controls.

Conventional therapeutic processes for the purification of blood extracorporeally include hemodialysis, ultrafiltration, plasmapheresis, hemoperfusion, plasma perfusion and combinations of these, i.e. hemofiltration, plasma exchange, hemodiafiltration and hemodialysis with sorbent regeneration of dialysate. Except for hemoperfusion, where blood is perfused through a column of selective sorbents directly (excepting those sorbents which are encapsulated by a membrane), all of the processes include a semipermeable membrane as an interface between the blood phase and the purification medium.

An electrolyte solution (dialysate solution) serves as the purification medium in hemodialysis. Ultrafiltration and plasmapheresis techniques do not utilize a purification medium. Rather, purification is done by removing a portion of fluid components from the blood plasma by filtration using transmembrane pressure difference as the driving force. Hemodialysis, ultrafiltration and plasmapheresis do not selectively remove specified components. Instead all components below the pore size of the membrane filter are removed by them. Hemodialysis and ultrafiltration use small pore size membranes which are below the size of plasma proteins (i.e. albumin has a mole weight of about 60,000 Daltons). On the other hand, plasmapheresis uses membranes with pore sizes greater than the size of plasma proteins so that large plasma components such as autoantibodies, immune complexes and viruses can be removed from the blood plasma. A distinct disadvantage in this process is that useful plasma components, such as certain proteins, enzymes and hormones, are also removed and lost.

In hemoperfusion and plasma perfusion techniques, selectivity is achieved by using selective sorbents for the binding of components to be removed from the blood. In plasma perfusion, plasma must first be separated from the blood by pumping blood through a membrane plasma filter or, in the alternative, a centrifuge is used to separate plasma from the blood. The plasma obtained as the filtrate or by decanting from the packed cells, is then pumped through a column of sorbents where the plasma is selectively depleted of components bound by the sorbents. The purified plasma is then combined with the filtered or precipitated blood cells and reinfused to the patient.

There are various prior art publications illustrative of the above methods or techniques. Shown in Ohnishi et al., U.S. Pat. No. 4,696,670 (1987) is a method where plasma is separated from blood. The plasma is perfused through a column of immobilized enzymes for the removal of low density lipoproteins (LDL). A complex switching method is used to implement the operation. Larson et al., U.S. Pat, No. 4,361,484 (1982) shows a method where an enzyme, antibody or protein A is immobilized in the pores of a membrane facing away from the blood phase by a chemical binding method. Using an oscillating pressure technique, plasma, or fluid is forced into and out of the membrane to achieve a high degree of convective mass transport. In Marconi et al., U.S. Pat. No. 4,248,704 (1981) a method is shown wherein an enzyme is trapped in a hollow fiber membrane to remove phenylalanine from the blood. This enzyme is impermeable to the membrane; however, phenylalanine permeates through the membrane where it is hydrolyzed by the enzyme.

Langer et al., U.S. Pat. No. 4,373,023 (1983) shows the use of immobilized heparinase on a support such as Sepharose, polyacrylamide or polyHEMA to degrade heparin in blood in an extracorporeal device prior to recirculating the blood to the patient. In this device the plasma is not separated and whole blood is brought into direct contact with the sorbent material.

Grossman, U.S. Pat. No. 3,742,946 (1973) shows a system for the treatment of renal failure which requires removal of the body's excess fluid and metabolic wastes. This system uses a semipermeable tubular membrane through which blood flows. The tubular membrane is surrounded by a closed shell containing a mixture of sorbents. One of the sorbents includes a desiccant which is stated to accelerate the convective transport of water across the membrane. This water gets absorbed and retained by the desiccant present in the shell. It is a objective of the Grossman procedure to retain this water in the shell chamber and not to reinfuse it to the patient. Water transport across the membrane in Grossman's procedure is by diffusion only.

A different system is shown by Skurkovich, U.S. Pat. No. 4,362,155 (1982). This system purifies blood or plasma in three steps which requires three subsystems, i.e. separation of plasma from blood using a plasma separator (filter), purification of the filtered plasma by pumping it through a mixture of sorbents contained in a packed column and reinfusion of the purified plasma to the patient by combining it with the filtered blood and reinfusion of the whole blood. This system is primarily for the removal of interferon and autoantibodies from whole blood or plasma. Nose' et al., U.S. Pat. No. 4,381,775 (1983) and Bensinger, U.S. Pat. No. 4,614,513 (1986) show processes similar to Skurkovich. Bensinger utilizes immobilized protein A sorbent for the removal of autoantibodies and immunoreactive agents from plasma.

Bernstein et al., U.S. Pat. No. 4,863,611 (1989) is directed to the removal of heparin from blood in an extracorporeal blood circulation system. In this system whole blood is in direct contact with a sorbent which may lead to problems such as thrombocytopenia, cellular damage, sorbent fine particle embolization, complement activation and the like. In this system blood is fluidized or recirculated at very high flow rates which leads to blood damage and particle fragmentation. A microemboli filter is required to catch these fine particles. Heparin removal by an immobilized heparinase enzyme sorbent is only about 20–60% of blood flow rate.

OBJECTIVES AND BRIEF SUMMARY OF THE INVENTION

It is an object of the present invention to provide a system and method of achieving both convective and diffusive transport of plasma across a filter membrane in a blood circulation system into a plasma chamber containing an electrolyte plasma chamber solution followed by the selective removal of plasma components using sorbents, immobilized enzymes or antibodies in the plasma chamber solution followed by the subsequent transport of the purified plasma across the filter membrane back into the blood.

It is also an object of the present invention to provide a system for purification of plasma in a blood circulation system wherein plasma components are filtered from the blood cells into a plasma chamber solution containing means for removing unwanted plasma components followed by repassage of the purified plasma back through the membrane into the blood wherein no oscillating blood flow conditions, plasma pump or transmembrane pressure controls are required.

A still further object of the invention is to provide a system for the removal of unwanted components from blood plasma, particularly heparin, in a blood circulation system wherein cellular components of the blood do not come into contact with the sorbents used for removing unwanted components and wherein the mechanism of mass transport for the passage of plasma components through a filter membrane used in the system are convective and diffusive transport and which does not require the presence of extraneous pumps or pressure control means.

These and other objects may be accomplished by means of pumping blood in a system through a specially designed "U" shaped hollow fiber membrane plasma filter immersed in a closed plasma chamber filled with a purifying medium containing sorbents, immobilized enzymes or antibodies in an electrolyte solution (e.g. a physiological saline solution). Preferably a bundle of hollow fibers is used as the filter and the blood flows in parallel through the fibers making up the bundle. As the blood flows through the entry arm of each "U" shaped hollow fiber membrane lumen, due to the positive transmembrane pressure difference (i.e., blood pressure in the lumen is greater than filtrate chamber pressure), plasma filtration through the entry arm into the plasma chamber takes place. The plasma entering the plasma chamber causes an increase in the plasma chamber pressure but does not exceed the pressure in the entry arm of the "U" shaped hollow fiber. The increase in pressure in the plasma chamber exceeds the blood pressure in the exit arm of the "U" shaped hollow fiber. That is, the transmembrane pressure difference is negative at the exit arm of the "U" shaped hollow fiber filter. Due to this negative transmembrane pressure difference, the direction of filtration reverses. That is, reverse filtration or reinfusion of plasma from the plasma chamber into the blood phase in the lumen of the exit arm of the "U"shaped hollow fiber. The described phenomena of positive filtration and reverse filtration from a "U" shaped hollow fiber filter establishes the circulation of plasma fluid in the plasma chamber. The plasma filtering through the entry arm of the "U" hollow fiber, which corresponds to the arterial end (or higher pressure region) passes through the plasma chamber solution containing the sorbents where plasma components or solutes get selectively depleted. The sorbents may be in any usable form of sufficient size that the sorbent is not permeable to the filter membrane, i.e. does not enter the blood. For example, sorbents may be in particulate form such as beads, spheres or the like. They may also be present as filaments or "angle hair" floating around the hollow fibers. Also, strands, sheets or films may be used as substrate sorbents. The form is not important as long as there is adequate opportunity for the circulation of plasma and contact between the sorbent in the plasma chamber solution and the plasma components to be removed. The purified plasma then reenters the blood phase in the exit arm of the "U" hollow fiber filters corresponding to the venous end (or low pressure region) where negative transmembrane pressure exists. Somewhere in the middle of the "U" hollow fiber the transmembrane pressure is zero, i.e. the blood pressure is the same as the pressure in the plasma chamber, and mass transport across the membrane in this region occurs by diffusion alone.

Throughout this disclosure, the term "plasma chamber solution" is used to signify the solution contained in the plasma chamber. At the beginning of a separation procedure the initial solution will comprise an electrolyte, i.e. saline, solution containing sorbents and any other desired materials. As the various plasma components enter the plasma chamber by convection o diffusion from the hollow fibers these will tend to equilibrate such that, excepting for the targeted components being bound to the sorbent in the plasma chamber, the concentration of the plasma components in the blood inside the lumen of the hollow fibers will be the same as the concentration of the same plasma components in the plasma chamber. Hence the makeup of the "plasma chamber solution" may vary during the removal and purification process but functionally the actual composition is not critical.

The invention is applicable to treating blood from any source. For example it may be the blood passing through any extracorporeal loop such as used in cardiopulmonary bypass surgery, blood coming from another machine or apparatus, blood coming out of storage and the like. The invention is more thoroughly and completely described by the drawings and detailed description which follow.

BRIEF DESCRIPTION OF THE DRAWINGS

FIG. 3 is a plan view of a "U" shaped hollow fiber filter immersed in a purifying medium such as a mixture of enzymes/sorbents in an electrolyte solution in a closed chamber showing entry and exit lines connecting the filter to what could be either an extracorporeal blood circulation system or for use in processing of stored blood and the like.

DETAILED DESCRIPTION OF THE INVENTION

Figure 1:
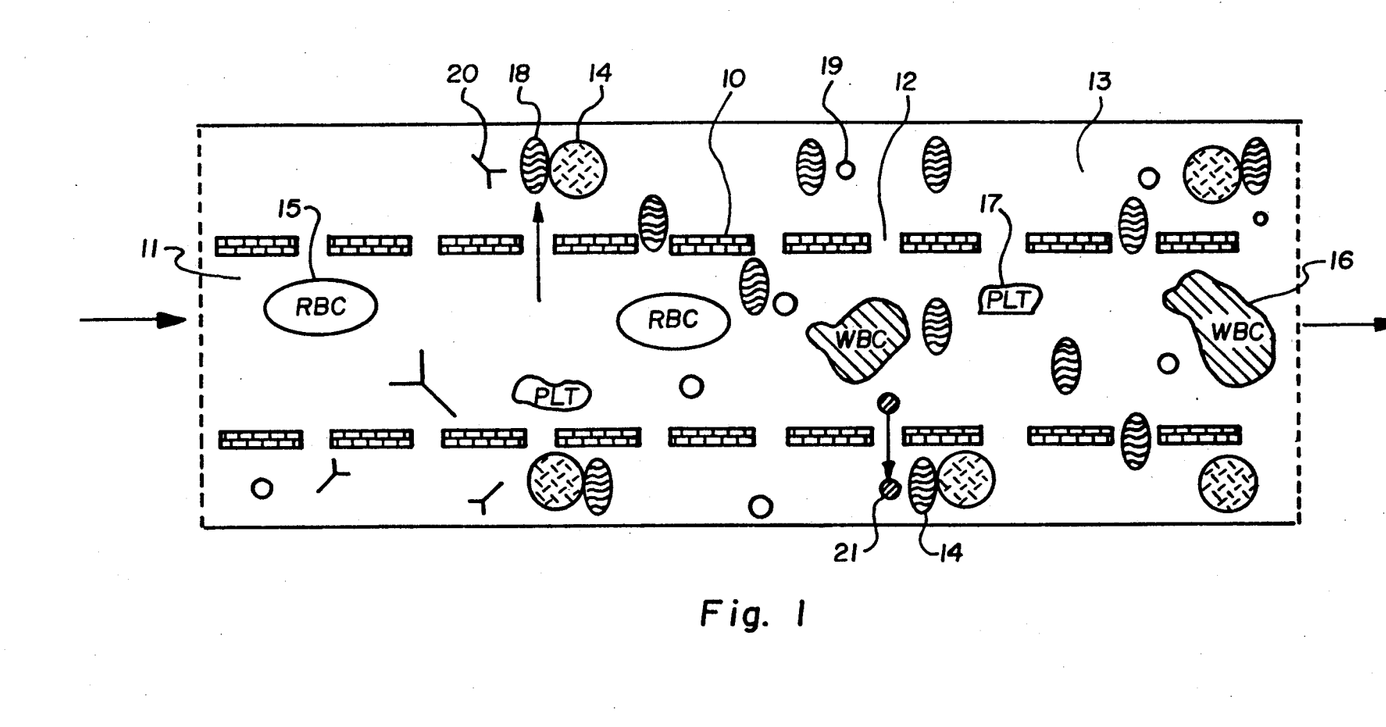
FIG. 1 is a schematic magnified representation of a single hollow fiber membrane showing heparinized blood passing through the lumen and the transport of plasma through pores in the membrane into surrounding filtrate solution containing sorbents for binding and removing the heparin.

There is illustrated in FIG. 1 the basic principle of plasma pheresis or plasma separation as utilized in the present invention. The hollow fiber membrane 10, actually a bundle of hollow fiber membranes which make up a filter, has a central lumen 11 through which the whole blood passes from the inlet to the outlet. The membrane 10 is porous having a series of pores or openings 12 through which plasma and plasma components, toxins, drugs or other solutes having diameters smaller than the pores can pass into a surrounding plasma chamber solution 13 containing a sorbent 14. The red blood cells 15, white blood cells 16, platelets 17 are of a size that they cannot pass through pores 12 and remain in the lumen 11 of the fiber 10. The plasma may contain various sugars, proteins, hormones, antibodies, fats, bile salts, toxins, electrolytes and the like as well as other substances which may have been administered for various purposes. Heparin, for example, is added to extracorporeal circulation circuits for its anticoagulant properties but is desirably removed and/or deactivated before leaving the extracorporeal loop and entering back into the in vivo blood circulation. In FIG. 1 there is shown particles representing heparin 18, and other plasma containing constituents 19, 20 and 21. When the heparin and other particles exit through pores 12 by diffusion or convection they enter into a plasma chamber solution 13 containing sorbent particles 14 which have a specificity for binding heparin 18 or other particles as desired. The heparin sorbent interaction will be explained in greater detail below.

Figure 2:
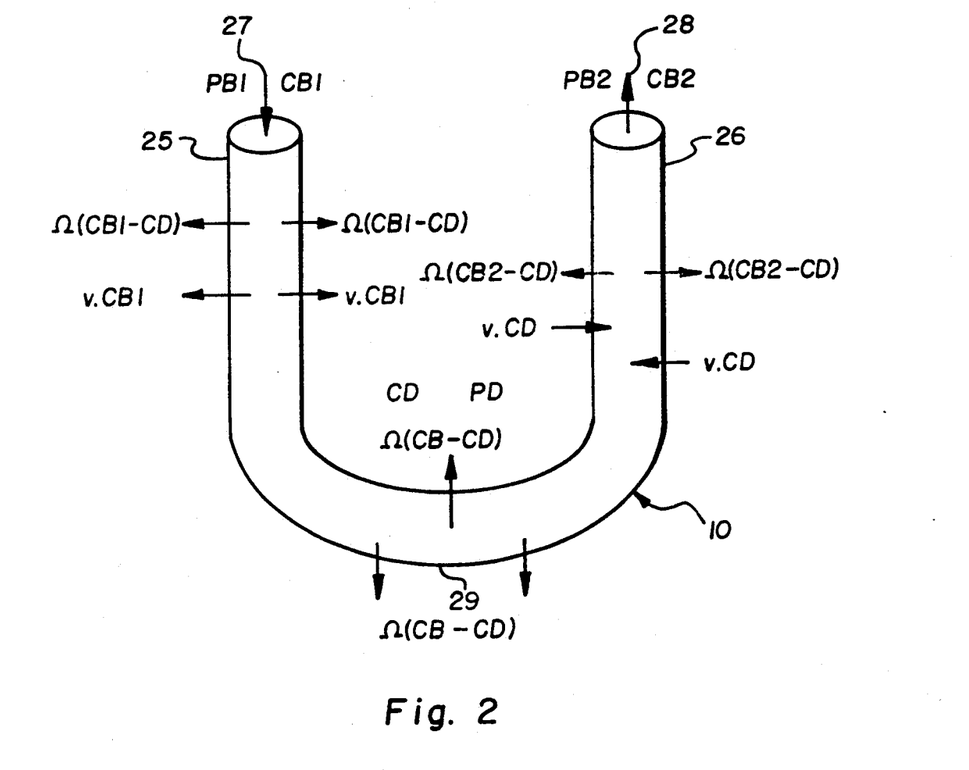
FIG. 2 is a schematic representation of a "U" shaped hollow fiber membrane showing the specific mass transport effects by which the exchange of heparin carrying plasma is transported from the lumen side of the membrane into the filtrate along the entry arm of the filter and deheparinized plasma is transported from the filtrate back to the lumen along the exit arm of the filter.

FIG. 2 schematically diagrams a single hollow fiber membrane 10 in the form of a "U" positioned in a closed plasma chamber (not shown) so as to be immersed in a plasma chamber solution. Thus, FIG. 2 illustrates the specific mass transport effects by which the exchange of heparin [or other components to be removed from the plasma] is able to be transported from the blood side, (i.e., using either in vivo or stored blood), of a fiber membrane along the inlet arm 25 of the fiber to a plasma phase by diffusion and convection where heparin [or other permeable components as desired] are removed by binding to a sorbent in the plasma chamber solution and the unbound plasma components are transported back across the membrane along the outlet arm 26 of the fiber to the blood side of the fiber membrane by convection. Blood flows through the lumen of the hollow fiber membrane in the path shown by the directional arrows 27 and 28. The plasma chamber is initially filled with an electrolyte solution mixed with enzymes, sorbents, living tissue, cells or fragments of tissue, immobilized enzymes or immobilized antibodies. For purposes of simplification, all of the binding agents which can be utilized to removed targeted plasma components in the plasma chamber are collectively referred to as "sorbents". In the preferred embodiment shown, the plasma chamber solution contains a sorbent which will bind heparin as will be more fully detailed below. For purposes of illustration it is assumed that there is complete mixing of components with the sorbent in the plasma chamber solution. This could be accomplished by use of mechanical agitation such as stirring or caused by magnetic or sonic techniques. Further, maximum mixing could be caused by improving convective aspects or internal circulation inside the plasma chamber by design. For example, a vortex could be created through reconfiguration of the hollow fibers within the plasma chamber or reconfiguration of the sorbents in the form of fibers, films, etc. could maximize mixing. The blood coming into the entry arm 25 of the "U" fiber is at the pressure designated as $PB_1$ and the concentration of solutes in the blood in the inlet arm 25 is designated as $CB_1$. Both the blood pressure (PB) and solute concentration (CB) in the lumen of the filter will vary along the filter as $PB_1$ changes to $PB_2$ and as $CB_1$ changes to $CB_2$, i.e. between the entry and outlet areas respectively. In other words, $PB_1$ and $PB_2$ [both being representations of PB] are variable along the length of the filter with $PB_1$ being greatest at the entrance 27 to inlet arm 25 and least at the point 29 where $PB_1$ equals PD (dialysate phase or plasma chamber solution pressure). Therefore, along the entry arm 25 the PB (shown as $PB_1$ in that area), while variable, is greater than at any other part of the "U" filter loop. The mass transfer of solutes in the blood from the entry arm 25 of the fiber to the plasma chamber occurs by both convection and diffusion. The mass transport by diffusion across the membrane for solutes in this area is concentration dependent, and it may be defined as $\Omega(CB_1-CD)$ where is the diffusive permeability (cm/sec) of the membrane for the solute and $CB_1$ is the solute concentration in the blood in entry arm area 25 of the hollow fiber and CD is the solute concentration in the plasma chamber. This is shown in FIG. 2 by a set of directional arrows along the entry arm 25. The velocity "v" of convection of fluid permeating through the pores of the membrane, and which will vary along the length of the membrane as blood pressure (PB) decreases from $PB_1$ to $PB_2$, depends upon the transmembrane membrane difference stated as PB−PD where PB is the blood pressure at any given reference area along the hollow fiber and PD is the pressure in the plasma or filtrate chamber which is almost constant throughout the chamber. When $PB_1 > PD$, the mass transfer of solutes from inside the lumen of the hollow fiber into the plasma chamber may be defined as $v \cdot CB_1$. Therefore, as long as PB>PD (i.e. when PB is $PB_1$) there will be mass transfer (MT) of solutes from within the lumen of the fiber to the plasma chamber solution by both convection and diffusion, i.e. $MT = \Omega(CB_1-CD) + v \cdot CB_1$. At some position 29 along the fiber as PB (blood pressure) decreases [shown in FIG. 2 as the bottom of the filter loop] PB and PD will equalize (PB≈PD) and there will be no transmembrane pressure difference and hence no driving force for the mass transfer of solutes by convection. At this area of the filter, the mass transport will therefore be present only by diffusion $\Omega(CB-CD)$ as indicated by the directional arrows in area 29 and this will be minimal if the concentration of solutes in the blood CB is the same as the concentration of solutes in the plasma chamber solution CD. As stated above, there is an incremental decrease in PB in the filter loop along inlet arm 25 as $PB_1$ decreases to PD and PB then becomes $PB_2$. When PB<PD, (i.e. when PB is $PB_2$) shown in FIG. 2 as being along the exit arm 26 of the filter loop, the mass transfer of solutes from the filter to the plasma chamber solution continues by diffusion as represented by $\Omega(CB_2-CD)$ and shown by directional arrows along exit arm 26. However, there is also a reverse mass transfer of solutes, which have not been selectively bound by the sorbent, from the plasma chamber solution back into the filter lumen by convection as represented by $v \cdot CD$ as also shown.

The significance of the mass transport in FIG. 2 shows that plasma solutes ca be filtered through a hollow porous fiber membrane into a plasma chamber where unwanted components can be removed by sorptive binding techniques and plasma and unbound solutes then reenter the hollow fiber based on mass transfer by diffusion and convection without the need for extraneous means such as oscillating blood flow conditions, plasma pumps or transmembrane pressure controls.

Figure 3:
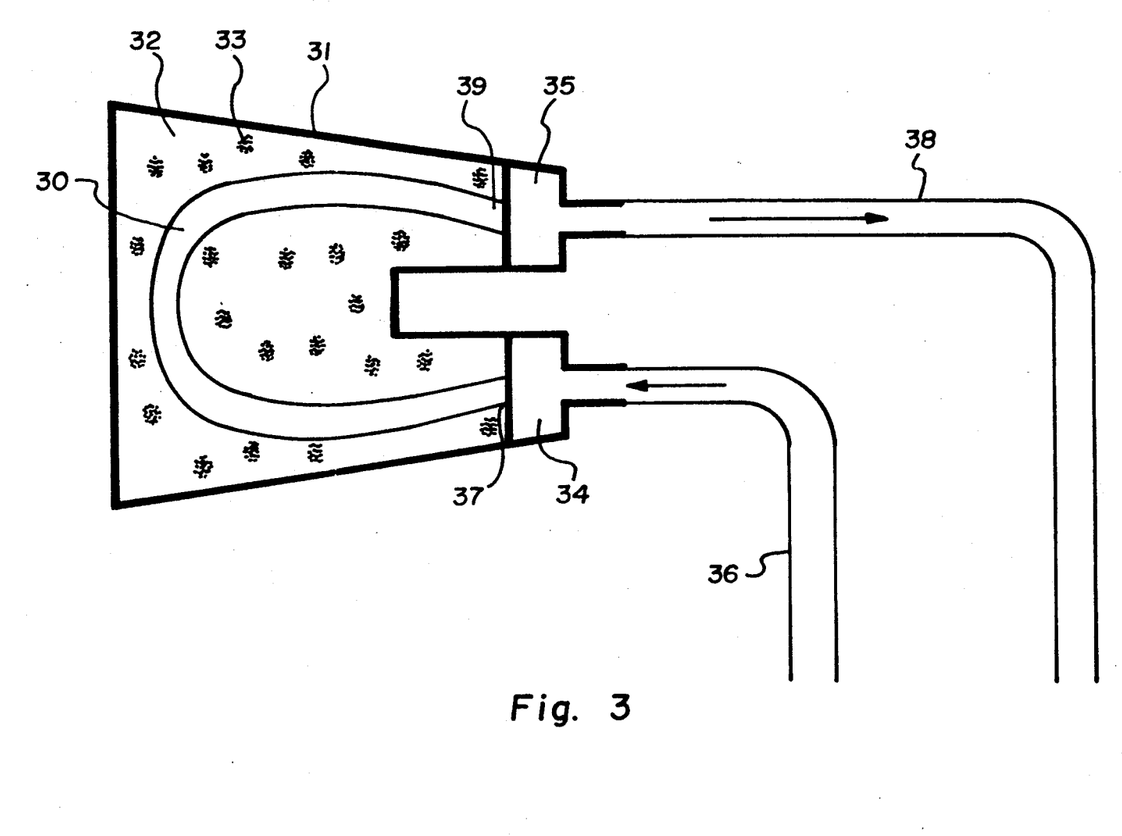

The overall system is represented in plan view in FIG. 3. A "U" shaped filter 30 is placed in a container 31 which is filled with plasma chamber solution 32 containing sorbents 33 for binding the desired solute, e.g. heparin. The container is closed by stoppers 34 and 35. An inlet line 36 connects with the entry end 37 of the filter loop in the vicinity of stopper 34. At the other side an outlet line 38 connects with the exit end of the filter in the vicinity of stopper 35. Either the ends of the lines 36 or 38 or the ends 37 and 39 of the filter pass through the stoppers in order to enable connections between the lines and the filter loop. Preferably lines 36 and 38 are shunt lines used in conjunction with an extracorporeal circuit.

As an example only and without intending to limit the invention, in the case of cardiopulmonary bypass surgery, the heparinized blood will pass through the device, after the bypass is completed in order to remove the heparin and avoid the requirement of administering protamine. In this regard lines 36 and 38 represent a dual flow cannula which could actually be a dual lumen single barrel cannula that could be inserted into the venous uptake incision of the cardiopulmonary bypass procedure. One tip of the dual flow cannula (line 36) would insert retrograde into the inferior vena cava and take up heparinized blood from the patient to the filter 30. A roller pump (not shown) would move blood under positive pressure to the plasma filter. Deheparinized blood is then returned to the patient via the dual flow cannula (line 38) and directed towards the right atrial inflow.

The hollow fiber membrane filter can be made of any blood compatible material having suitable pore size to allow passage of desired solute materials into the plasma chamber, even those of high molecular weight, and yet retain the blood cells and platelets in the lumen of the hollow fiber. Pore sizes in the membrane are relatively large with sizes ranging between about $0.01\mu$ to $1.0\mu$ being suitable with pore sizes of about $0.1\mu$ to $0.8\mu$ being preferable. Exemplary of suitable fiber materials are polypropylene, cellulose diacetate, polycarbonate, polyvinylchloride, polyvinylalcohol, polymethylmethacrylate, polyethylene, polyethylenevinylalcohol and the like.

The hollow fiber filter dimensions (hollow fiber lumen diameter, length of each hollow fiber and the number of fibers) and the blood flow rate through the fiber have to be optimized based on the art of membrane plasma separation and enzyme engineering. It is well known in the art of membrane plasma separation that the plasma separation rate is directly proportional to the blood shear rate and the transmembrane pressure. However, damage to the blood cells may occur if the transmembrane pressure is increased beyond a particular limit. Also, blood cells are susceptible to high shear rate. For a given blood flow rate and total membrane surface area, transmembrane pressure increases: (i) with the increase in hollow fiber length and (ii) with the decrease in lumen size. Shear rate also increases with the decrease in lumen size. The above factors may be considered in arriving at the optimum size of the hollow fiber filter. The weight of adsorbed or enzymes to be taken in the plasma chamber may be determined based on the well known art of enzyme engineering. The removal rates of solutes from the blood depends upon the plasma separation rate, and the amount [weight, surface area, etc.] and affinity of sorbents. Hollow fibers of the filter having inside diameters of between about $150\mu$ and $500\mu$ and wall thicknesses of between about $50\mu$ to $400\mu$ are typical. The internal surface area of a typical filter may be between about 0.1 and 5.0 $m^2$ and the volume of the plasma chamber may be between about 50 and 1000 mls. The length of the filter from the inlet port to the exit port should be between about 10 and 100 cm with lengths of about 20 to 25 cm being preferred. Flow rates of blood through the filter may vary from about 50 to 3000 ml/min.

The plasma chamber 31 should be sized to hold an adequate amount of sorbent materials to bind the unwanted plasma solutes such as heparin. This may vary depending on the surgical procedure for which an extracorporeal system is being used and the amount of heparin or other material to be removed and nature of sorbent material.

A commercial filter bundle mounted in a plasma chamber is available as a unit from Organon Teknika N.V. under the Curesis Plasma Separator tradename. This unit is a disposable hollow fiber membrane-type plasma separator consisting of a microporous polypropylene hollow fiber bundle mounted in polyurethane exit ports and plastic housing made of polystyrene. Blood enters the fiber bundle through the blood inlet port, passes through the hollow fiber lumens in which a positive transmembrane pressure allows plasma to pass through the porous hollow fiber membrane along its entire length into the plastic housing where it exits through the plasma port. The plasma lean blood exits the blood outlet port.

This unit can be modified for use in the present invention by prefilling the plasma chamber with plasma chamber solution containing sufficient sorbent particles to bind the plasma component to be separated and closing the plasma exit port. The unit as thus modified is then suitable for use as a simultaneous plasma purification and reinfusion system having the above described advantages.

The removal of heparin from an extracorporeal circuit is a primary objective of the invention. The binding of heparin to a solid substrate by affinity adsorption techniques is documented in the art. The prior art cited above gives several examples. Also, Mohammad et al, "Quantitative Removal of Heparin from Plasma and Other Aqueous Solutions by Affinity Adsorption on Poly(L)lysineSepharose 4B", Thrombosis Research 20: 599–609 (1980) is illustrative of the activity of poly(L-)lysine agarose beads as one form of preferred sorbents.

The invention is applicable to any plasma sorbent system where separation, interaction and recombination takes place. Thus any system where plasma is separated from whole blood, plasma components are interacted with sorbent and the plasma (minus the interacted components) are recombined with the blood is within the scope of the invention. Typical surgical procedures where blood is heparinized include cardiopulmonary bypass, hemodialysis, angioplastic procedures, plasmapheresis, autotransfusion and hemoconcentration. Exemplary of other potential applications of the system are: (1) the removal of autoantibodies using sorbents such as immobilized Protein-A; (2) removal of circulating toxins and tumor antigens using sorbents such as immobilized monoclonal antibodies and specific immobilized ligands; (3) removal of protein bound toxins and drugs (e.g., in the case of drug overdose); (4) procedures using live cells in the plasma chamber in the place of sorbents such as islet cells or liver tissue fragments for the treatment of diabetes, hepatocytes for the treatment of hepatic failure and the like; (5) selective removal of plasma components using immobilized enzymes as sorbents and (6) removal of cholesterol (low density lipoproteins, LDL) using sorbents specific to LDL.

In vitro Application

The following examples demonstrate the preferred embodiment of removing heparin from aqueous solutions and/or plasma using poly(L)lysine Sepharose CL-4B as the sorbent. In each example the filter device used was a commercial Curesis Plasma Separator modified to close the plasma chamber. The chamber contained 200 mls of a plasma chamber solution in which was suspended sorbent beads as described in each example. The filter device dimensions were 120 ×110×56 mm. The "U" filter consisted of a bundle made up of polypropylene microporous hollow fibers having an internal diameter of 330 μm, a wall thickness of 150 μm, a maximum pore size of 0.65 μm and having an effective surface area of 0. 12 m$^2$. The priming volume of the fiber lumens, i.e. "blood compartment" was 14 ml. The inlet of the filter was connected by plastic tubing to a "source", i.e. simulated blood solution or extracorporeally to a test animal, and fed via roller pump at the flow rate shown in each example.

EXAMPLE 1

Using a simple in vitro system and simulated "blood", this example demonstrates variation in inlet blood pressure (PB1), outlet blood pressure (PB2) and plasma pressure (PD) obtained by circulating a physiological buffer solution containing a known amount of heparin, as a "blood solution", through the "U" shaped hollow fiber filter device described above. The plasma chamber contained 200 mls of a buffer solution consisting of phosphate buffered saline (P.B.S.) containing 8.52 gm. sodium phosphate, 5.44 gm. potassium phosphate and 2.20 gm sodium chloride in 1 liter of water. The pH is adjusted to pH of 7.4 by drop-wise titration with 7 M NaOH. The outlet pressure (PB2) was maintained at a constant value (atmospheric pressure).

TABLE 1

| Flow Rate | Pressure (mm/Hg) | | |
|---|---|---|---|
| (mm/min) | PB1 | PD | PB2 |
| 100 | 0 | 0 | 0 |
| 150 | 5 | 0 | 0 |
| 200 | 15 | 0 | 0 |
| 250 | 20 | 0 | 0 |
| 280 | 35 | 0 | 0 |
| 300 | 47 | 8 | 0 |
| 350 | 65 | 20 | 0 |
| 400 | 75 | 30 | 0 |
| 450 | 90 | 40 | 0 |
| 500 | 105 | 50 | 0 |
| 550 | 130 | 65 | 0 |

The above data show that the inlet blood pressure (PB1) increases with the increase in blood flow rate through the filter lumen. The pressure in the plasma phase (PD) also increases proportionately, while the outlet blood pressure (PB2) is maintained at a constant value. As shown in Table 1, PD remains equal to PB2 (zero) until PB1 exceeds PB2 by about 35 mm Hg. This occurs at a flow rate corresponding to a typical in vivo blood flow rate of about 280/min. The difference between PB1 and PD is a direct measure of the driving force for the filtration rate of fluid from the blood phase in the inlet arm of the filter into the plasma phase. This driving force (PB1−PD) is seen to be increasing with the increase in the blood flow rate. As shown, the driving force increased from 45 mm Hg to 65 mm Hg as the "blood" flow rate was changed from 400 ml/min to 550 ml/min. This test demonstrates that, as PD increases with the increase in PB1 for flow rates greater than 280 ml/min, two different regions of mass transfer are created. In the inlet arm of the filter where PB>PD, there is a positive convection of mass transfer across the membrane through its pores (=v. CB) into the plasma chamber solution. However, in the outlet arm of the filter where PB<PD this causes a negative or reverse convective mass transfer across the membrane through its pores (=v. CD) from the plasma chamber solution into the lumen.

EXAMPLE 2

Using the same system as used in Example 1 this example is designed to demonstrate variations in heparin concentrations "blood" in the inlet (CB1) and outlet (CB2) portions of the "U" filter and also in the plasma chamber solution phase (CD) as a function of time. The "blood" was 5 liters of heparin containing phosphate buffered saline (PBS) and flowed through the filter at a rate of 300 ml/min. The "blood" solution was recirculated through the filter over a 65 minute period of time. At 50 minutes the flow was reversed by switching the inflow and outflow ports. The heparin concentration was assayed with Azure II dye. This is accomplished by mixing 5 mg of Azure II dye (Sigma #A 2507) with 250 mls of deionized water to provide a final concentration of 0.02 mg/ml. A 0.5 ml sample to be assayed is added to 4.5 mls of the Azure II solution and allowed to incubate for 60 second. Absorbance is measured in a spectrophotometer at a wavelength of 500 nanometers and compared against a known calibration standard curve to determine heparin concentration. The plasma chamber solution was a buffer solution containing 30.1 grams of poly-L-lysine derivatized agarose [Pharmacia, Sepharose 4B-CL] beads having a diameter of between about 30–140 microns and a total minimum heparin binding capacity of about 25,000 units. There was no agitation of the sorbent in the plasma chamber solution during the test. The heparin concentration (in units) monitored at the inlet (CB1), outlet (CB2) and plasma chamber solution (CD) as a function of time are given in Table 2.

TABLE 2

| | Heparin Concentration (u/ml) | | |
|---|---|---|---|
| Time (min) | CB1 | CD | CB2 |
| 1 | 4.20 | 0.10 | 3.20 |
| 2 | 4.25 | 0.80 | 3.25 |
| 3 | 3.75 | 1.10 | 2.90 |
| 4 | 4.05 | 1.90 | 3.10 |
| 5 | 4.10 | 2.35 | 3.10 |
| 7 | 4.00 | 2.50 | 3.40 |
| 10 | 3.80 | 3.00 | 2.70 |
| 15 | 3.70 | 3.60 | 2.80 |
| 20 | 3.60 | 3.50 | 2.90 |
| 25 | 3.45 | 3.40 | 2.80 |
| 30 | 3.25 | 3.45 | 2.80 |
| 40 | 3.10 | 3.20 | 2.75 |
| 50 | 2.85 | 2.85 | 2.50 |
| 55 | 2.75 | 0.70 | 2.20 |
| 60 | 2.70 | 0.75 | 2.15 |
| 65 | 2.40 | 0.85 | 1.95 |

As can be seen from Table 2, the heparin level CB1) in the recirculating "blood" flowing in at the inlet of the filter decreased from 4.2 u/ml to 2.7 u/ml over a period of 60 minutes recirculation. The heparin level in the plasma chamber solution phase (CD) increased to almost the same level as CB1 after 15 minutes and CB1 and CD remained substantially equal from 15 to 50 minutes when agitation was created in the plasma chamber solution phase by switching the inflow and outflow ports. During the 15 to 50 minute time period, the mass transfer by diffusion $[=\Omega(CB-CD)]$ was almost zero because CB (heparin concentration in the inlet arm of the filter) was almost equal to CD (heparin concentration in the plasma chamber solution). However, the convective mass transfer ($=v.CB$) of heparin from the inlet arm of the filter into the plasma chamber solution phase was not zero during this period as seen by the continued decline in CB1 and CB2. Due to the convective flow of fluid in the plasma chamber from the inlet region of the filter to the outlet region, sorbent beads moved away from the inlet region and accumulated adjacent the filter at the outlet region. This caused a nonuniform distribution of sorbents in the plasma chamber. This phenomena decreased the adsorption rate of heparin by the sorbents in the plasma chamber. In actual use the sorbents would be more evenly distributed by a stirring mechanism or other means of agitation in of the plasma chamber solution. When the inlet and outlet ports were switched at the 50 minute time period, the sorbents were redistributed due to the change of direction of convective flow of plasma in the plasma chamber whereupon the heparin (CD) in the plasma chamber solution was more rapidly bound to the sorbents causing a significant drop in CD.

EXAMPLE 2A

This example shows the effect of mechanical agitation of the sorbent beads in an identical procedure to that described in Example 2. Table 2A shows the results of heparin concentration CB1, CD and CB2 when agitated at different time intervals as indicated.

TABLE 2A

| Time (min) | Heparin Concentration (u/ml) | | |
|---|---|---|---|
| | CB1 | CD | CB2 |
| 0 | 4.06 | 0.00 | 0.00 |
| 1 | 3.99 | 0.80 | 2.92 |
| 3 | 3.57 | 1.99 | 3.28 |
| 5 | 3.57 | 2.98 | 3.10 |
| 7 | 3.57 | 1.86 | 2.86 |
| 10 | 3.51 | 0.74 | 2.75 |
| 15 | 3.10 | 0.92 | 2.75 |
| 20 | 3.22 | 0.98 | 2.63 |
| 25 | 3.16 | 1.21 | 2.63 |
| 28* | 3.16 | 1.09 | 2.51 |
| 30 | 2.80 | 0.00 | 2.21 |
| 40 | 2.67 | 0.15 | 1.92 |
| 50* | 2.21 | 0.86 | 1.86 |
| 55 | 1.92 | 0.00 | 1.57 |

*Mechanical Agitation

As can be seen from Table 2, the mechanical agitation of the filter causes a resuspension of the sorbent beads within the dialysate chamber creating a more uniform distribution of the sorbent and resulting in a marked decrease in heparin concentration in the dialysate chamber and a subsequent decrease in the outflow heparin concentration thereby improving the overall heparin removal rate when utilizing the device.

Techniques other than mechanical agitation can be effectively utilized to improve the uniformity of distribution of sorbent beads within the chamber to take advantage of convective flow of plasma such as reconfiguring the hollow fiber arrangement from a "U" shape to a closed loop or loops as in a coil. As used herein, the term "U" shaped filter, hollow fiber and the like is meant to encompass any functional hollow fiber or hollow fiber bundle configuration, such as a "U", coil, loop, or any other configuration having inlet and outlet areas and through which blood may circulate provided plasma components may exit the hollow fiber lumens into a plasma chamber solution and then reenter back into the hollow fibers in the manner described herein. Reconfiguration of the plasma chamber, mechanical perturbation of beads within the plasma chamber either by internal or external means and/or modification of sorbent bead density and/or size which would enhance suspension of the sorbent in the plasma preventing it from packing or settling out of suspension. Additional methods might also include reconfiguration of the sorbent material itself such as Macroporus ($\geq 1$ mm) trabeculated substrates, membranous fibers ($\geq 0.5$ micron) or fibrous strands or filaments ($\geq 0.5$ microns) which would all have the same surface structure and chemical structure and properties that the bead material has. The purpose would be to create a surface area for the poly-L-lysine coupled surface to be uniformly distributed in such a manner to allow intimate and unrestricted flow of plasma in the dialysate chamber thereby allowing maximum binding of heparin or other desired solutes to the substrate and return of plasma back through the hollow fiber outflow to recombine with the whole blood.

In vivo Application

The following examples show results of an animal study using the filter device described above forming an extracorporeal circuit in a carotid-jugular bypass shunt of a sheep. In Example 3 plain sepharose CL-4B beads were used as the sorbent in the plasma chamber. Example 4 shows the same arrangement used in Example 3 with the exception that poly(L)lysine derivatized CL-4B sepharose beads were utilized in the plasma chamber. Example 5 is similar to Example 4 except that a dual lumen single barrel catheter was used to form beginning and end of the extracorporeal loop. The following parameters are applicable to all three examples. The sheep weighed approximately 72 kgs. and received an initial heparin dose of 350 Units/kg. i.e. 25,300 Units of heparin at $-10$ minutes of beginning the bypass. The heparin is administered via bolus intravenous injection into the jugular vein. At $-8$ minutes the first blood sample was taken to determine heparin concentration. The extracorporeal circuit was made up of 0.25"$\times$0.375" PVC tubing with the venous uptake cannula being inserted into the inferior Vena caVa and the return cannula directing the flow to the right atrium. The total extracorporeal blood circuit volume was about 130 ml. with the filter per se having a volume of abut 14 ml. The plasma chamber on the plasma chamber solution side of the filter had a volume of about 220 mls. The blood circulation through the filter device was controlled by a roller pump upstream of the filter device and was maintained at 300 ml/min. The results of each study are given individually in the Examples which follow.

EXAMPLE 3

The plasma chamber contained a phosphate buffered saline (P.B.S.) as in Example 1 holding approximately 75 grams of plain sepharose CL-4B beads having a diameter of between about 60 and 140 microns. The bypass through the extracorporeal circuit was maintained for 60 minutes with blood samples being taken at the inlet (CB1) and the outlet (CB2) of the filter at periodic intervals to determine heparin concentration as follows in Table 3.

TABLE 3

| Time (min) | Heparin Concentration (u/ml) | |
| --- | --- | --- |
| | CB1 | CB2 |
| −20 | 4.5 | — |
| 1 | 4.3 | 4.6 |
| 5 | 4.0 | 3.6 |
| 10 | 3.9 | 3.9 |
| 15 | 4.0 | 4.2 |
| 20 | 3.7 | 4.5 |
| 30 | 4.1 | 4.1 |
| 45 | 4.2 | 4.2 |
| 60 | 4.3 | — |

This device showed no decrease in heparin concentration after 60 minutes of bypass and upon conducting blood coagulation assays showed no presence of fibrin clots.

EXAMPLE 4

The plasma chamber contained the same plasma chamber solution as in Example 3 except that approximately 80 grams of poly(L)lysine derivatized sepharose CL-4B beads having a diameter between about 60 and 140 microns were utilized in the place of plain sepharose. The bypass through the extracorporeal circuit was maintained for only 25 minutes with blood samples being taken at the both the inlet and outlet ports of the filter at periodic intervals to determine heparin concentration as follows in Table 4.

TABLE 4

| Time (min) | Heparin Concentration (u/ml) | |
| --- | --- | --- |
| | CB1 | CB2 |
| −5 | 4.0 | — |
| 1 | 3.6 | 3.5 |
| 5 | 3.2 | 2.6 |
| 10 | 2.6 | 2.4 |
| 15 | 2.8 | 2.2 |
| 20 | 2.2 | 1.9 |
| 25 | 1.9 | 1.7 |

Using the standard curve generated during the control study of Example 3, the heparin concentration in this example was reduced by over 75% within the first 25 minutes and the heparin concentration on the inflow side (representing systemic plasma concentration of the animal) of the device went to 2.0 μ/ml at about 20 minutes as well. Blood coagulation assays completed upon conclusion of the bypass revealed the presence of fibrin clots indicating the positive effects of heparin removal.

EXAMPLE 5

As indicated above. This example is essentially the same as Example 4 with the exception of the tubing used to form the extracorporeal loop. This test was actually a continuation of the bypass operation started in Example 4. The bypass in Example 4 was terminated after 25 minutes. The new device was surgically attached to the junction of the superior vena cava and the inferior vena cava near the right atrium via a dual lumen cannula which allowed uptake of systemically heparinized blood from the inferior vena cave and delivered it to the heparin removal device, returning blood back through to the return lumen of the cannula delivering deheparinized blood to the right atrium while an additional 16,800 Units of heparin was administered 90 minutes after the initial 25,200 unit dose. The bypass through the extracorporeal circuit was maintained for 45 minutes with blood samples being taken at the both the inlet and outlet ports of the filter at periodic intervals to determine heparin concentration as follows in Table 5.

TABLE 5

| Time (min) | Heparin Concentration (u/ml) | |
| --- | --- | --- |
| | CB1 | CB2 |
| −2 | 7.5 | — |
| 2 | 7.4 | 4.8 |
| 5 | 6.5 | 4.8 |
| 10 | 5.6 | 4.0 |
| 15 | 5.2 | — |
| 20 | 4.5 | 3.4 |
| 30 | 3.4 | 2.5 |
| 45 | 2.0 | — |
| 60 | 1.9 | — |

Using the standard curve generated during the control study of Example 3, the heparin concentration in this example was back to baseline on the outflow side of the filter device within 30 minutes and the heparin concentration on the inflow side of the device went below 0.5 u/ml at about 40 minutes. Blood chemistry assays completed upon conclusion of the bypass revealed the presence of fibrin clots again indicating the positive effects of heparin removal.

While the preferred embodiments of the invention have been illustrated and described, it should be understood that variations, whether or not apparent to those skilled in the art, may be made and still be within the scope of the invention. One embodiment not specifically illustrated but contemplated is to intimately combine the fiber and sorbent material into a single composite substrate instead of having the sorbent contained in the plasma chamber solution. The sorbent could be an integral part of or attached to the fiber materials. Accordingly, the invention is not to be limited to the specific embodiments as shown herein but are to be determined by reference to the appended claims and the functional equivalents thereof.

We claim:

1. A blood circulation and filtration system for the selective removal of targeted plasma components from blood by means of convective and diffusive transport of plasma from said blood across a filter membrane into a plasma chamber solution where the selective removal of targeted plasma components from non-targeted plasma components using sorbents in the plasma chamber solution is accomplished followed by the subsequent transport of the non-targeted plasma components across the filter membrane back into the blood which comprises:

(a) a closed plasma chamber filled with an electrolyte plasma chamber solution containing one or more sorbents which have an affinity for and bind said targeted plasma components said closed plasma chamber being configured to freely circulate, equilibrate, mix and interact plasma components with said sorbents in said plasma chamber solution under relatively uniform pressure, (b) a "U" shaped hollow fiber membrane plasma filter having an inlet arm and an outlet arm immersed in said plasma chamber solution in said closed plasma chamber, (c) means for securing said inlet arm and outlet arm of said fiber filter in said plasma chamber and losing said chamber to maintain relatively uniform plasma chamber solution pressure, (d) circulation means for directing said blood into said inlet arm, through said filter and out through said outlet arm.

2. A system according to claim 1 wherein said hollow fiber membrane plasma filter consists of a bundle of parallel hollow fibers.

3. A system according to claim 2 wherein said sorbents are of a size and configuration that said sorbents are not permeable to the filter membrane.

4. A system according to claim 3 wherein the hollow fibers making up said filter membrane are constructed of a blood compatible material having a suitable pore size to allow passage of plasma into the plasma chamber solution while retaining blood cells and platelets from the blood within the hollow fibers.

5. A system according to claim 4 wherein the pore sizes in said membrane range between about $0.01\mu$ to $1.0\mu$.

6. A system according to claim 5 wherein hollow fibers are made from a material selected from the group consisting of polypropylene, cellulose diacetate, polycarbonate, polyvinylchloride, polyvinylalcohol, polymethylmethacrylate, polyethylene and polyethylenevinylalcohol.

7. A system according to claim 5 wherein the hollow fibers making up the filter must have a lumen diameter and overall length to allow appropriate amounts of blood to be directed through the filter for a length of time to allow sufficient amounts of plasma to pass from the inlet arm of the filter into the plasma chamber solution and the non-targeted plasma components to pass back into the outlet arm of the filter.

8. A system according to claim 7 wherein said hollow fibers have inside diameters of between about 150 and $500\mu$ and wall thicknesses of between about 50 to $400\mu$.

9. A system according to claim 8 wherein the internal surface area of said filter membrane is between about 0.1 and 5.0 $m^2$.

10. A system according to claim 8 wherein the length of the filter is between about 10 and 100 cm.

11. A system according to claim 10 wherein the sorbent in said plasma chamber is in the form of particles, filaments, strands or sheets.

12. A system according to claim 11 wherein the sorbent is a member selected from the group consisting of enzymes, living tissue, fragments of tissue, cells, and immobilized enzymes or antibodies.

13. A system according to claim 11 wherein the sorbent is in the form of particles and has affinity for heparin.

14. A system according to claim 13 wherein the sorbent is agarose.

15. A system according to claim 14 wherein the sorbent is a poly-L-lysine derivatized agarose.

16. A blood circulation and filtration system for the selective removal of targeted plasma components from blood by means of convective and diffusive transport of plasma from said blood across a sorbent containing filter membrane into a plasma chamber solution where the selective removal of targeted plasma components from non-targeted plasma components using sorbents in said filter membrane is accomplished followed by the subsequent transport of the non-targeted plasma components across the filter membrane back into the blood which comprises:

(a) a closed plasma chamber filled with an electrolyte plasma chamber solution, said closed plasma chamber being configured to freely circulate, equilibrate and interact plasma components in said plasma chamber solution under relatively uniform pressure, (b) a "U" shaped hollow fiber membrane plasma filter containing one or more sorbents which have an affinity for and bind said targeted plasma components having an inlet arm and an outlet arm immersed in said plasma chamber solution in said closed plasma chamber, (c) means for securing said inlet arm and outlet arm of said fiber filter in said plasma chamber and closing said chamber to maintain relatively uniform plasma chamber solution pressure, (d) circulation means for directing said blood into said inlet arm, through said filter and out through said outlet arm.

17. A method for the selective removal of targeted plasma components from blood which comprises (a) providing a blood circulation and filtration system having (1) a closed plasma chamber filled with an electrolyte plasma chamber solution containing one or more sorbents which have an affinity for and bind said targeted plasma components, (2) a "U" shaped hollow fiber membrane plasma filter having an inlet arm and an outlet arm and immersed in said plasma chamber solution in said closed plasma chamber, (3) means for securing said inlet arm and outlet arm of said fiber filter in said plasma chamber and closing said chamber, (4) circulation means for directing blood into said inlet arm, through said filter and out through said outlet arm;

(b) directing blood by said circulation means from a source into said inlet arm, through said filter and out said exit arm at a volume and velocity which permits the convective and diffusive transport of plasma from said blood across said filter membrane along the inlet arm of said filter into said plasma chamber solution, (c) causing said plasma in said plasma chamber solution to come into contact with said sorbents where said targeted plasma components are selectively bound to said sorbents; and (d) causing said non-targeted plasma components to pass by diffusive and convective transport from said plasma chamber solution across the filter membrane back into the blood along the outlet arm of said filter and out of said system.

18. A method according to claim 17 wherein cellular components of the blood do not enter the plasma chamber solution or come into contact with the sorbents and wherein the passage of plasma components through said filter membrane is accomplished by convective and diffusive transport in the absence of extraneous pressure control means.

19. A method according to claim 18 wherein the transmembrane pressure difference of the blood in the entry arm of the filter is greater than pressure in the plasma chamber and wherein the plasma entering the plasma chamber from said inlet arm causes a pressure increase in the plasma chamber which does not exceed the pressure in said entry arm of filter but wherein the increase in pressure in the plasma chamber exceeds the transmembrane pressure in the outlet arm of the filter.

20. A method according to claim 19 wherein the blood source contains heparin which is a targeted plasma component.

21. A method according to claim 20 wherein the sorbent in said plasma chamber has a binding affinity for heparin.

22. A method according to claim 21 wherein the sorbent is agarose.

23. A method according to claim 22 wherein the sorbent is a poly-L-lysine derivatized agarose.

* * * * *